(12) United States Patent
Smith

(10) Patent No.: US 9,872,723 B2
(45) Date of Patent: Jan. 23, 2018

(54) SURGICAL INSTRUMENTS, SYSTEMS, AND METHODS INCORPORATING WIRELESS BI-DIRECTIONAL COMMUNICATION

(71) Applicant: COVIDIEN LP, Mansfield, MA (US)

(72) Inventor: Robert B. Smith, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 700 days.

(21) Appl. No.: 14/259,819

(22) Filed: Apr. 23, 2014

(65) Prior Publication Data

US 2015/0088115 A1  Mar. 26, 2015

Related U.S. Application Data

(60) Provisional application No. 61/881,536, filed on Sep. 24, 2013.

(51) Int. Cl.
| | | |
|---|---|---|
| *H02J 7/00* | (2006.01) | |
| *A61B 18/14* | (2006.01) | |
| *H02J 50/12* | (2016.01) | |
| *H02J 50/40* | (2016.01) | |
| *A61B 18/12* | (2006.01) | |

(Continued)

(52) U.S. Cl.
CPC .......... *A61B 18/1445* (2013.01); *A61B 18/12* (2013.01); *A61B 18/1206* (2013.01); *H02J 7/0004* (2013.01); *H02J 7/025* (2013.01); *H02J 50/10* (2016.02); *H02J 50/12* (2016.02); *H02J 50/40* (2016.02); *H02J 50/80* (2016.02); *A61B 2017/0046* (2013.01); *A61B 2017/00221* (2013.01); *A61B 2017/00734* (2013.01); *A61B 2018/1226* (2013.01)

(58) Field of Classification Search
CPC .................................................. A61B 18/1445
USPC .................................................. 320/108, 112
See application file for complete search history.

(56) References Cited

U.S. PATENT DOCUMENTS

| | | | |
|---|---|---|---|
| 3,690,313 A | 9/1972 | Weppner et al. | |
| 6,326,884 B1 | 12/2001 | Wohlrabe | |
| (Continued) | | | |

FOREIGN PATENT DOCUMENTS

| | | |
|---|---|---|
| EP | 1943958 A1 | 7/2008 |
| EP | 2218409 A1 | 8/2010 |
| (Continued) | | |

OTHER PUBLICATIONS

European Search Report from corresponding EP 14186187.2 dated Feb. 16, 2015.

(Continued)

*Primary Examiner* — Richard V Muralidar

(57) ABSTRACT

A surgical system and method is provided generally including a portable surgical instrument, a battery assembly, and a battery charger. The battery assembly is removably coupled to the portable surgical instrument and is configured to wirelessly transfer electrical power to the portable surgical instrument. The battery assembly is also removably couplable to the battery charger and is configured to wirelessly transfer electrical power to the battery charger and wirelessly receive electrical power from the battery charger. The portable surgical instrument and the battery charger are configured for simultaneous bi-directional communication of data with the battery assembly via the transferred or received electrical power.

20 Claims, 7 Drawing Sheets

(51) Int. Cl.
*H02J 7/02* (2016.01)
*H02J 50/10* (2016.01)
*H02J 50/80* (2016.01)
*A61B 17/00* (2006.01)

(56) References Cited

U.S. PATENT DOCUMENTS

| | | | |
|---|---|---|---|
| 8,443,476 | B2 | 5/2013 | Hilscher et al. |
| 2008/0167671 | A1 | 7/2008 | Giordano et al. |
| 2010/0114090 | A1 | 5/2010 | Hosier |
| 2011/0071520 | A1 | 3/2011 | Gilbert |
| 2011/0204119 | A1 | 8/2011 | McCuen |
| 2011/0208170 | A1 | 8/2011 | Hafner et al. |
| 2011/0248668 | A1* | 10/2011 | Davis .................. H01M 10/48 320/106 |
| 2013/0075443 | A1 | 3/2013 | Giordano et al. |
| 2013/0079790 | A1* | 3/2013 | Stein .................. A61F 2/4611 606/102 |
| 2015/0088115 | A1 | 3/2015 | Smith |

FOREIGN PATENT DOCUMENTS

| | | |
|---|---|---|
| JP | 2004-135245 A | 4/2004 |
| JP | 2011-67631 A | 4/2011 |
| JP | 2012-187408 A | 10/2012 |
| JP | 2015-523848 A | 8/2015 |
| WO | 2008/017041 A2 | 2/2008 |

OTHER PUBLICATIONS

European Search Report dated May 22, 2017, for Application No. 16203121, 9 pages.

Japanese Office Action dated Sep. 20, 2017, for JP Application No. 2016-238594 with English Translation (10 pages).

* cited by examiner

SURGICAL INSTRUMENTS, SYSTEMS, AND METHODS INCORPORATING WIRELESS BI-DIRECTIONAL COMMUNICATION

CROSS REFERENCE TO RELATED APPLICATION

The present application claims the benefit of and priority to U.S. Provisional Application Ser. No. 61/881,536, filed on Sep. 24, 2013, the entire contents of which are incorporated herein by reference.

BACKGROUND

Technical Field

The present disclosure relates to devices, systems, and methods for wireless bi-directional communication between a battery assembly and one or more target devices.

Background of Related Art

Battery-powered devices are advantageous in that they obviate the need for cables coupling the device to an electrical outlet or external power source. A typical battery pack for a battery-powered device includes one or more battery cells coupled to one another via a powering circuit that provides electrical power to the device. The battery pack includes electrical contacts, for example, gold plated contacts, that mate with corresponding contacts on a charger or a battery-powered device to create an electrical connection between the battery pack and the charger or battery-powered device. Power is provided across the contacts for charging and/or providing power to the battery-powered device, e.g., for activating an electrosurgical or ultrasonic generator of a battery-powered surgical instrument. Communication between the battery pack and the charger or battery-powered device is also typically performed through the electrical connection formed by the electrical contacts.

SUMMARY

The systems and methods according to aspects of the present disclosure provide simultaneous bi-directional communication between a battery assembly and a charger or surgical instrument.

In accordance with aspects of the present disclosure, a surgical system is provided generally including a portable surgical instrument and a battery assembly. The battery assembly is removably coupled to the portable surgical instrument and configured to wirelessly transfer electrical power to the portable surgical instrument. The portable surgical instrument and the battery assembly are configured for simultaneous bi-directional communication of data via the transferred electrical power.

In some aspects of the present disclosure, the battery assembly includes a first winding and the portable surgical instrument includes a second winding. The first and second windings together form a transformer for transferring the electrical power from the battery assembly to the portable surgical instrument when the battery assembly is coupled to the portable surgical instrument.

In some aspects of the present disclosure, the communication of data in a direction from the battery assembly to the surgical instrument is performed by adjusting the transferred electrical power in a first manner and the communication of data in a direction from the surgical instrument to the battery assembly is performed by adjusting the transferred electrical power in a second, different manner.

In some aspects of the present disclosure, the battery assembly is configured to transmit data to the portable surgical instrument in the first manner by shifting a phase of the transferred electrical power and the portable surgical instrument is configured to detect the phase shift and decode the transmitted data from the phase shift.

In some aspects of the present disclosure, the portable surgical instrument includes a phase-shift keying detector for detecting the phase shift of the transferred electrical power.

In some aspects of the present disclosure, the portable surgical instrument is configured to transmit data to the battery assembly in the second manner by modulating an amplitude of the transferred electrical power. The battery assembly is configured to detect the modulated amplitude and decode the transmitted data from the modulated amplitude of the transferred electrical power.

In some aspects of the present disclosure, the battery assembly includes an amplitude modulation detector for detecting the amplitude modulation of the transferred electrical power.

In some aspects of the present disclosure, the transferred electrical power is a power square wave.

In some aspects of the present disclosure, the surgical system further includes a battery charger. The battery assembly is removably couplable to the battery charger and configured to at least one of wirelessly transfer electrical power to the battery charger and wirelessly receive electrical power from the battery charger. The battery charger and the battery assembly are configured for simultaneous bi-directional communication of data via the transferred or received electrical power.

In some aspects of the present disclosure, the battery assembly includes a first winding and the battery charger includes a second winding. The first and second windings together form a transformer for transferring the electrical power from the battery assembly to the battery charger and from the battery charger to the battery assembly when the battery assembly is coupled to the battery charger.

In accordance with aspects of the present disclosure, a battery assembly couplable to a target device is provided generally including a battery cell, a first winding, and battery circuitry. The first winding is electrically connected to the battery cell and is alignable relative to a second winding of the target device to form a transformer. The battery circuitry is electrically connected to the battery cell and to the first winding and is configured to control at least one of the transfer of electrical power from the battery cell across the transformer to the target device and the reception of electrical power from the target device across the transformer to the battery cell. The battery circuitry is configured for simultaneous bi-directional communication of data with the target device via the transferred or received electrical power.

In some aspects of the present disclosure, the battery circuitry is configured to transmit data to the target device by shifting a phase of the transferred electrical power.

In some aspects of the present disclosure, the battery circuitry is configured to transmit data to the target device by modulating the amplitude of the received electrical power.

In some aspects of the present disclosure, the battery circuitry is configured to receive data from the target device by detecting a phase shift of the received electrical power and decoding the data from the detected phase shift.

In some aspects of the present disclosure, the battery circuitry includes a phase-shift keying detector for detecting the phase shift of the received electrical power.

In some aspects of the present disclosure, the battery circuitry is configured to receive data from the target device by detecting an amplitude modulation of the transferred electrical power and decoding the data from the detected amplitude modulation.

In some aspects of the present disclosure, the battery circuitry includes an amplitude modulation detector for detecting the amplitude modulation of the transferred electrical power.

In some aspects of the present disclosure, the transferred electrical power and the received power are power square waves.

In some aspects of the present disclosure, the target device is selected from a group consisting of a surgical instrument and a battery charger.

In accordance with aspects of the present disclosure, a method of simultaneous bi-directional communication between a battery assembly and a target device includes coupling the battery assembly to the target device, wirelessly transferring electrical power from one of the battery assembly and the target device to the other of the battery assembly and the target device, and simultaneously transferring data from the battery assembly to the target device and from the target device to the battery assembly via the transferred electrical power by: phase shifting the transferred electrical power by the one of the battery assembly and the target device; amplitude modulating the transferred electrical power by the other of the battery assembly and the target device; detecting the phase shifting of the transferred electrical power by the other of the battery assembly and the target device; and detecting the amplitude modulation of the transferred electrical power by the one of the battery assembly and the target device.

Any of the above aspects of the present disclosure, to the extent consistent, may be combined without departing from the scope of the present disclosure.

BRIEF DESCRIPTION OF THE DRAWINGS

Various aspects of the present disclosure are described hereinbelow with reference to the drawings, wherein.

DETAILED DESCRIPTION

Figure 3:
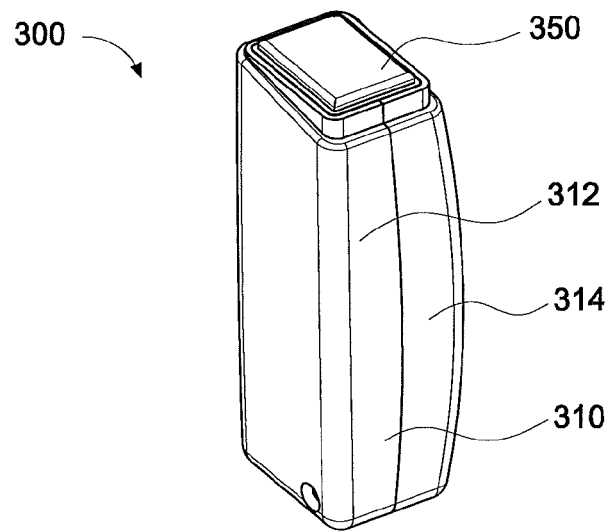
FIG. 3 is a side, perspective view of a battery assembly configured for use with the surgical system of FIG. 1.
Figure 4:
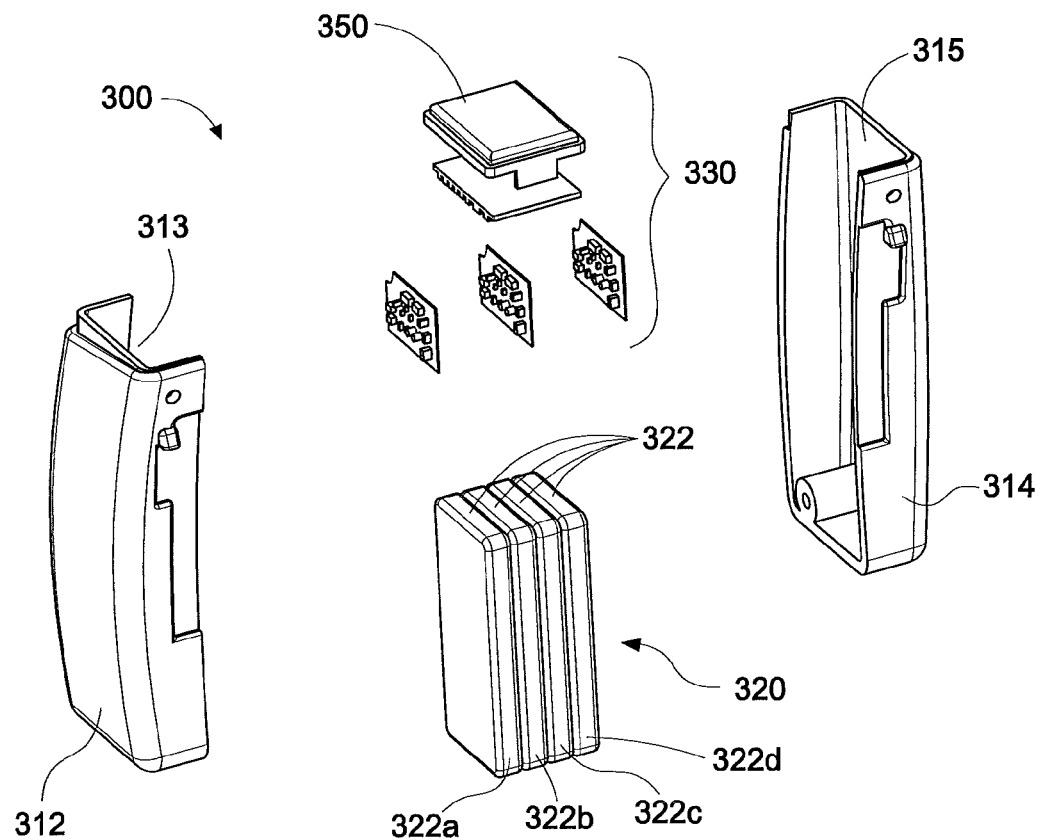
FIG. 4 is an exploded, perspective view of the battery assembly of FIG. 3.
Figure 5:
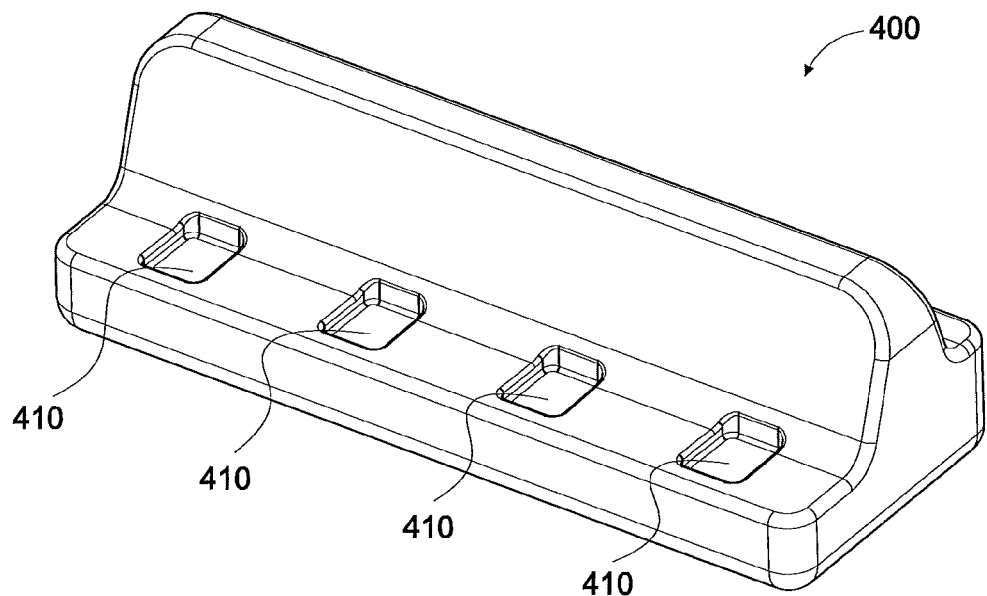
FIG. 5 is a side, perspective view of a battery charger configured for use with the surgical system of FIG. 1.
Figure 6:
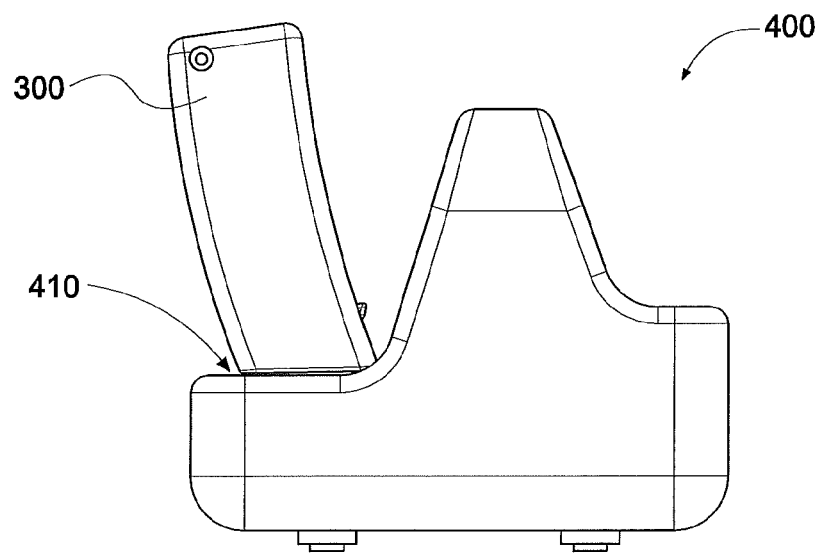
FIG. 6 is a side view of the battery charger of FIG. 5.

Referring now to FIGS. 1-8, a surgical system 10 provided in accordance with the present disclosure generally includes a portable, battery-powered surgical instrument 20, a rechargeable battery assembly 300 (FIGS. 3 and 4), and a battery charger 400 (FIGS. 5 and 6). Surgical system 10 is configured to permit simultaneous bi-directional communication between rechargeable battery assembly 300 and one or more target devices, e.g., surgical instrument 20 and battery charger 400, for example, using phase shifting and amplitude modulation of a power square wave transferred across a transformer. Although phase shifting and amplitude modulation are disclosed with respect to the exemplary embodiments detailed herein, other suitable configurations and/or methods of wireless data transmission are also contemplated. As detailed below, battery assembly 300 is configured to removably couple to both surgical instrument 20 and battery charger 400 in electrical communication therewith via transformers 42 (FIG. 7) and 52 (FIG. 8), respectively, to provide inductive transfer of energy and simultaneous bi-directional communication. Other suitable loads for electrical coupling to battery assembly 300 are also contemplated including, for example, computers, robotic systems, other instruments, etc.

Figure 1:
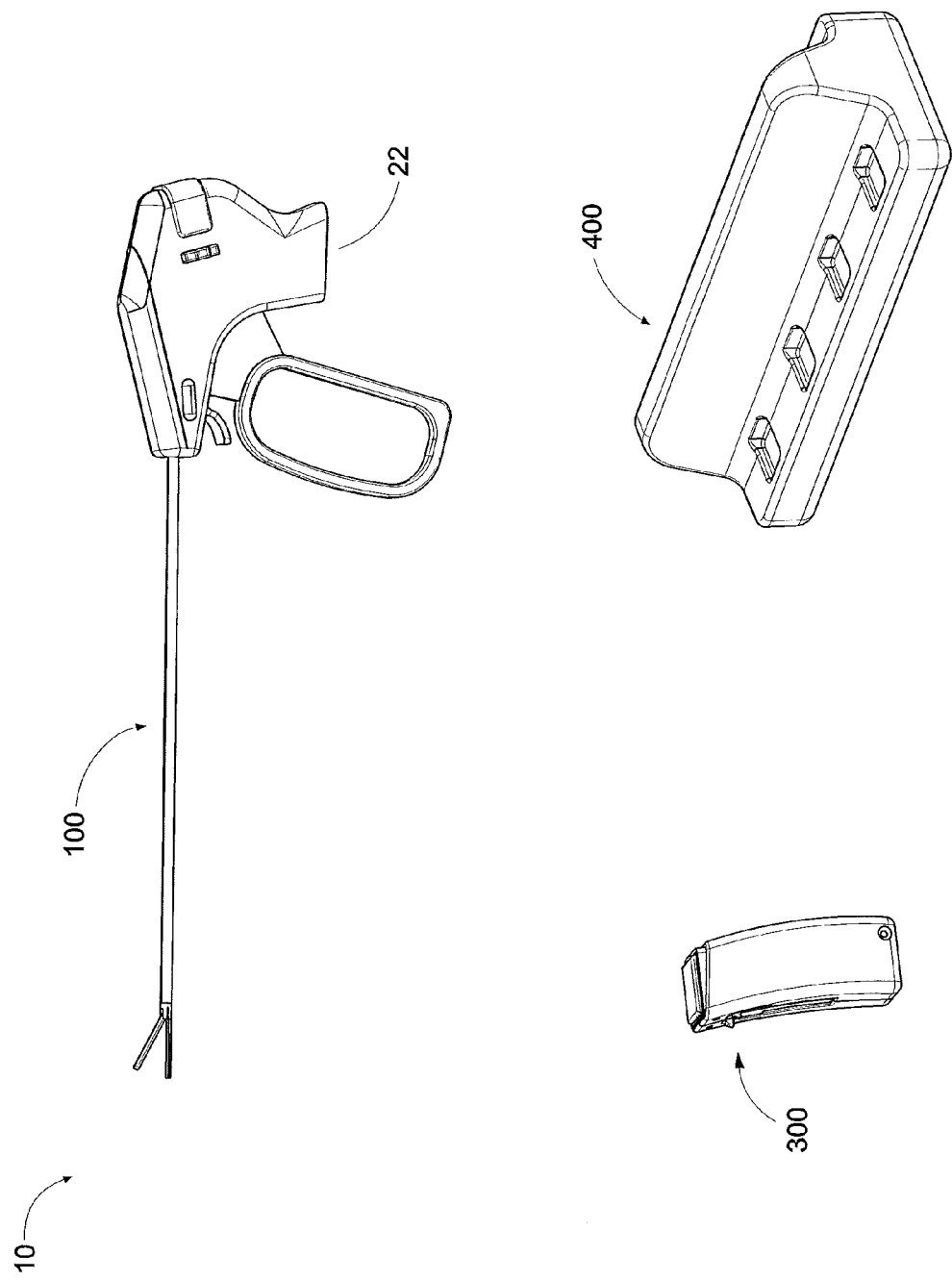
FIG. 1 is a side, perspective view of a surgical system provided in accordance with the present disclosure.
Figure 2A:
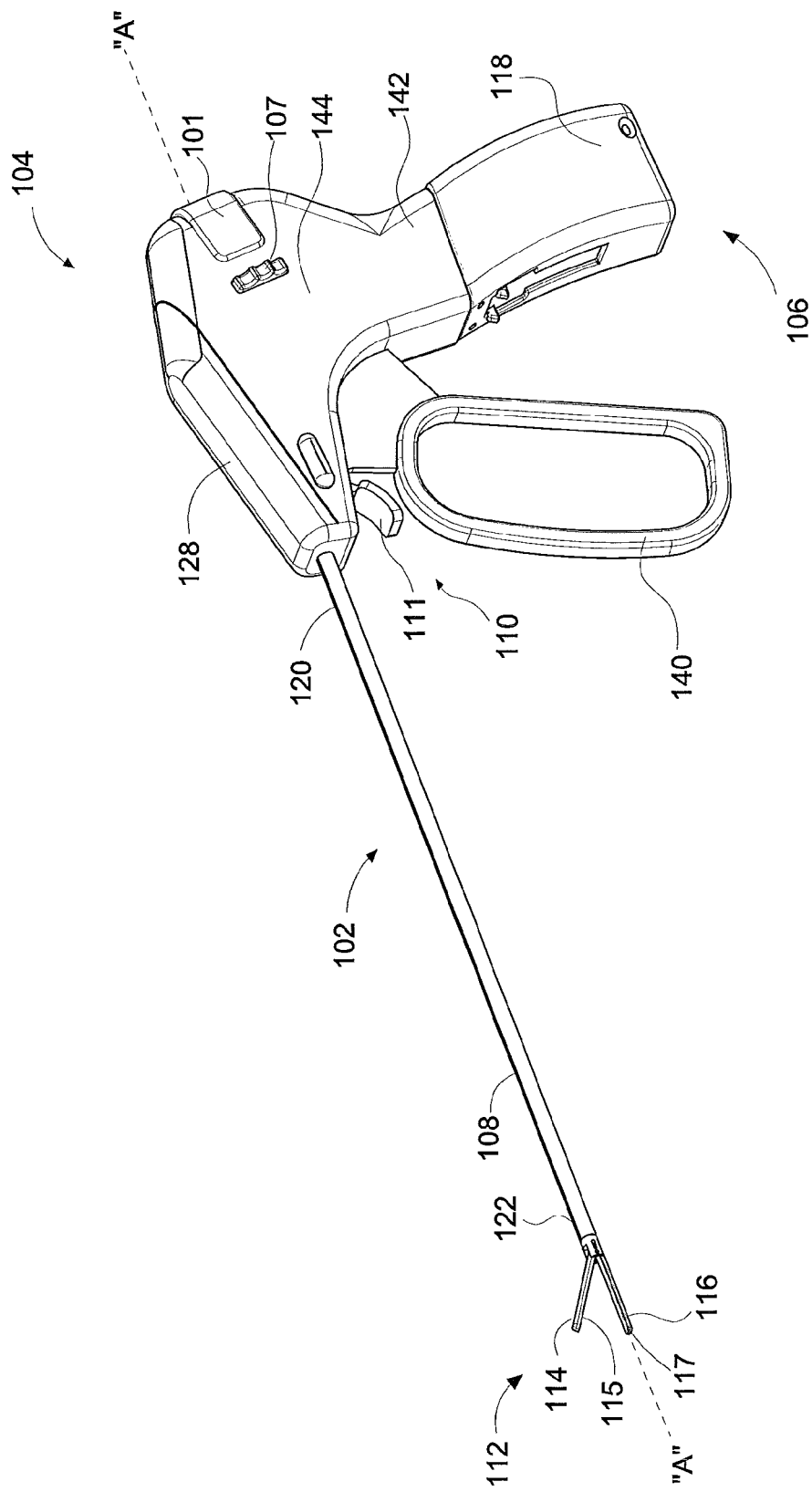
FIG. 2A is a side, perspective view of a portable, battery-powered surgical instrument configured for use with the surgical system of FIG. 1.
Figure 2B:
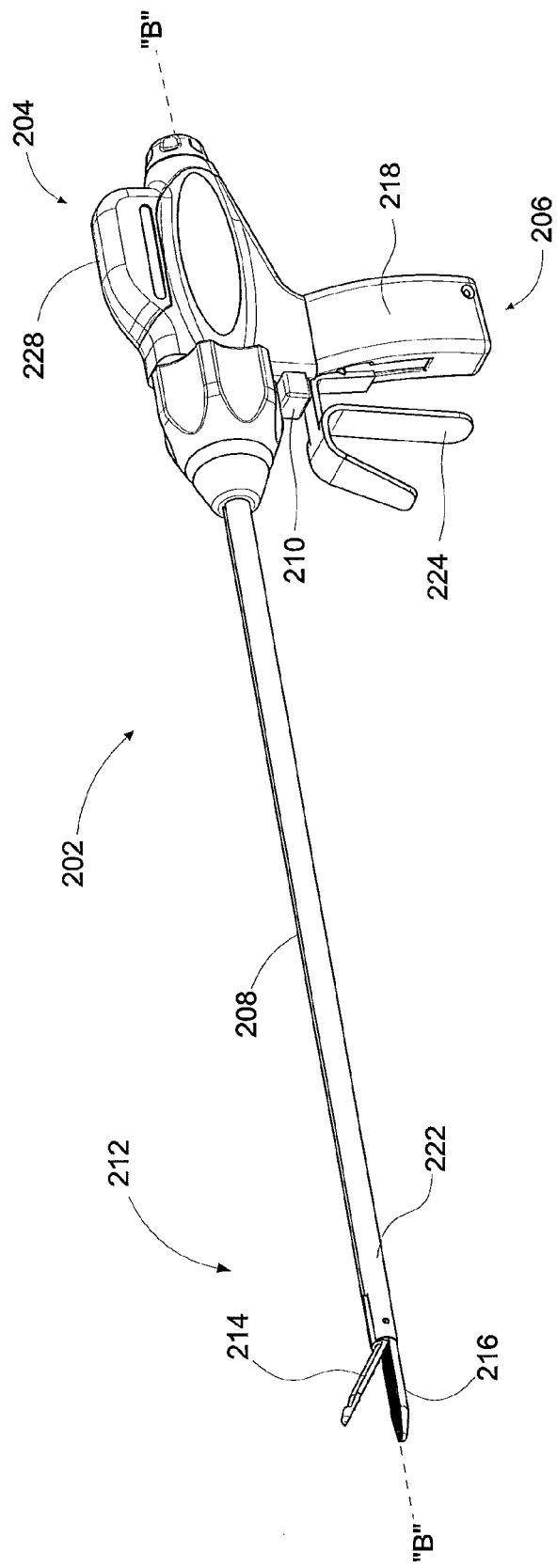
FIG. 2B is a side, perspective view of another portable, battery-powered surgical instrument configured for use with the surgical system of FIG. 1.

Surgical instrument 20 may be for example, a portable, battery-powered electrosurgical instrument 102, as shown in FIG. 2A, a portable, battery-powered ultrasonic surgical instrument 202, as shown in FIG. 2B, or any other suitable battery-powered device such as a handheld tool, electronic device, or the like. As can be appreciated, different considerations apply to each particular type of device; however, the features and aspects of the present disclosure are equally applicable and remain generally consistent with respect to any suitable battery-powered device. For the purposes herein, electrosurgical instrument 102 and ultrasonic instrument 202 are generally described.

With reference to FIG. 2A, electrosurgical instrument 102, shown as an electrosurgical forceps, generally includes a housing 104, a handle assembly 106, a rotating assembly 107, a shaft 108, a trigger assembly 110, a drive assembly (not shown), an end effector assembly 112, a battery assembly 118, and an electrosurgical generator 128. End effector assembly 112 operatively connects to handle assembly 106 via the drive assembly (not shown) for imparting movement of one or both of jaw members 114, 116 of end effector assembly 112 between a spaced-apart position and an approximated position for grasping tissue therebetween.

Continuing with reference to FIG. 2A, shaft 108 is coupled to housing 104 at proximal end 120 thereof and extends distally from housing 104 to define a longitudinal axis "A-A." End effector assembly 112, including jaw members 114 and 116, is disposed at a distal end 122 of shaft 108. End effector assembly 112 is shown configured as a unilateral assembly wherein jaw member 116 is fixed relative to shaft 18 and jaw member 114 is pivotable relative to jaw member 116 and shaft 108 between the spaced-apart and approximated positions. However, this configuration may be reversed, e.g., wherein jaw member 114 is fixed relative to shaft 108 and jaw member 116 is pivotable relative to jaw member 114 and shaft 108. Alternatively, end effector assembly 112 may be configured as a bilateral assembly, e.g., wherein both jaw members 114, 116 are pivotable relative to one another and shaft 8 between the spaced-apart and approximated positions.

Electrosurgical instrument 102 may be configured as a bipolar instrument. That is, each of the jaw members 114, 116 may include a respective seal plate 115, 117 that is configured to function as an active (or activatable) and/or return electrode. Each seal plate 115, 117 is electrically coupled to generator 128 via one or more electrical leads (not shown) that extend from generator 128, through shaft 108, eventually coupling to one or both of seal plates 115, 117 for conducting energy through tissue grasped therebetween. However, forceps 102 may alternatively be configured as a monopolar instrument.

Handle assembly 106 includes a moveable handle 140 that is movable relative to fixed handle portion 142 for moving jaw members 114, 116 of end effector assembly 112 between the spaced-apart and approximated positions. Rotating assembly 107 is rotatable in either direction about longitudinal axis "A-A" to rotate shaft 108 and, thus, end effector assembly 112 about longitudinal axis "A-A." Trigger assembly 110 is in operable communication with a knife assembly (not shown) including a knife blade (not shown) that is selectively translatable between jaw members 114, 116 to cut tissue grasped therebetween, e.g., upon actuation of trigger 111 of trigger assembly 110.

With continued reference to FIG. 2A, housing 104 is configured to releasably engage electrosurgical generator 128 and battery assembly 118. Generator 128 is releasably engagable with body portion 144 of housing 104, while battery assembly 118 is releasably engagable with fixed handle portion 142 of housing 104. More specifically, battery assembly 118 is configured to engage fixed handle portion 142 of housing 104 such that battery assembly 118 functions as the stationary handle of housing 104 to facilitate grasping of the forceps 102. Generator 128 releasably engages body portion 144 of housing 104 and may be selectively removable from body portion 144 either in connection with the removal of battery assembly 118 or independently.

When forceps 102 is assembled, generator 128 is disposed in operable communication with battery assembly 118 to provide electrosurgical energy to end effector 112 for electrosurgically treating tissue, e.g., to seal tissue, although forceps 102 may alternatively be configured to deliver any other suitable form of energy to tissue, e.g., thermal energy, microwave energy, light energy, etc. With respect to electrosurgical tissue treatment, generator 128 may include suitable electronics that convert the electrical energy from battery assembly 118 into an RF energy waveform to energize one or both of jaw members 114, 116. That is, generator 128 may be configured to transmit RF energy to seal plate 115 of jaw member 114 and/or seal plate 117 of jaw member 116 to conduct energy therebetween for treating tissue. Activation switch 101 disposed on housing 104 is activatable for selectively enabling generator 128 to generate and subsequently transmit RF energy to seal plate 115 and/or seal plate 117 of jaw members 114, 116, respectively, for treating tissue grasped therebetween.

Referring now to FIG. 2B, ultrasonic instrument 202 includes components similar to that of forceps 102 shown in FIG. 2A, namely, a housing 204, a handle assembly 206, a shaft 208, an end effector assembly 212, a battery assembly 218, and a generator 228. Accordingly, only the differences between ultrasonic instrument 202 and forceps 102 (FIG. 2A) will be described in detail below.

Housing 204 is configured to releasably engage ultrasonic generator 228 and battery assembly 218. Shaft 208 extends distally from housing 204 to define longitudinal axis "B-B" and includes end effector assembly 212 disposed at distal end 222 thereof. One or both of jaw members 214 and 216 of end effector assembly 212 are movable relative to one another, e.g., upon actuation of moveable handle 224, between an open position and a clamping position for grasping tissue therebetween. Further, one of the jaw members, e.g., jaw member 216, serves as an active or oscillating ultrasonic blade that is selectively activatable to ultrasonically treat tissue grasped between jaw members 214, 216.

Generator 228 includes a transducer (not shown) configured to convert electrical energy provided by battery assembly 218 into mechanical energy that produces motion at the end of a waveguide, e.g., at jaw member 216. More specifically, the electronics (not explicitly shown) of the generator 228 convert the electrical energy provided by battery assembly 218 into a high voltage AC waveform that drives the transducer (not shown). When the transducer (not shown) and the waveguide are driven at their resonant frequency, mechanical, e.g., ultrasonic, motion is produced at the active jaw member 216 for treating tissue grasped between jaw members 214, 216. Further, an activation button 210 disposed on housing 204 is selectively activatable to operate instrument 202 in two modes of operation: a low-power mode of operation and a high-power mode of operation.

Referring to FIGS. 3 and 4, features and aspects of the present disclosure are described with respect to exemplary battery assembly 300. The aspects and features of exemplary battery assembly 300 are equally applicable for use with battery assembly 118 (FIG. 2A) of forceps 102 (FIG. 2A), battery assembly 218 (FIG. 2B) of forceps 202 (FIG. 2B), or any other suitable battery assembly configured for use with a battery-powered device.

Battery assembly 300 generally includes an outer housing 310, a battery pack 320, battery circuitry 330, and an interface cap 350. Outer housing 310 is formed from first and second housing parts 312, 314 that cooperate to house battery pack 320 and battery circuitry 330. Housing parts 312, 314 define cut-outs 313, 315, respectively, that cooperate to form a window configured to retain interface cap 350. In some embodiments, first and second housing parts 312, 314 and interface cap 350 may be monolithically formed about battery pack 320 and battery circuitry 330 for example, by overmolding or the like. Battery assembly 300 may be hermetically sealed to inhibit chemical and fluid ingress into the battery assembly during use or sterilization.

With continued reference to FIG. 4, battery pack 320 includes one or more battery cells 322, e.g., lithium polymer battery cells or other suitable battery cells, and, in some embodiments, four battery cells 322a, 322b, 322c, and 322d, although greater or fewer battery cells 322 are also contemplated. Battery cells 322 provide DC voltage to battery circuitry 330 which converts the DC voltage to AC voltage for output across transformers 42 (FIG. 7) and 52 (FIG. 8), as will be detailed below.

Referring now to FIGS. 5 and 6, battery charger 400 includes one or more charging bays 410 for receiving the interface cap 350 of battery assembly 300, and charging circuitry 420 (FIG. 8) configured to transmit and receive power, control signals and/or otherwise communicate with the battery assembly 300 via charging bays 410 when the interface cap 350 is received within one of the charging bays 410.

Figure 7:
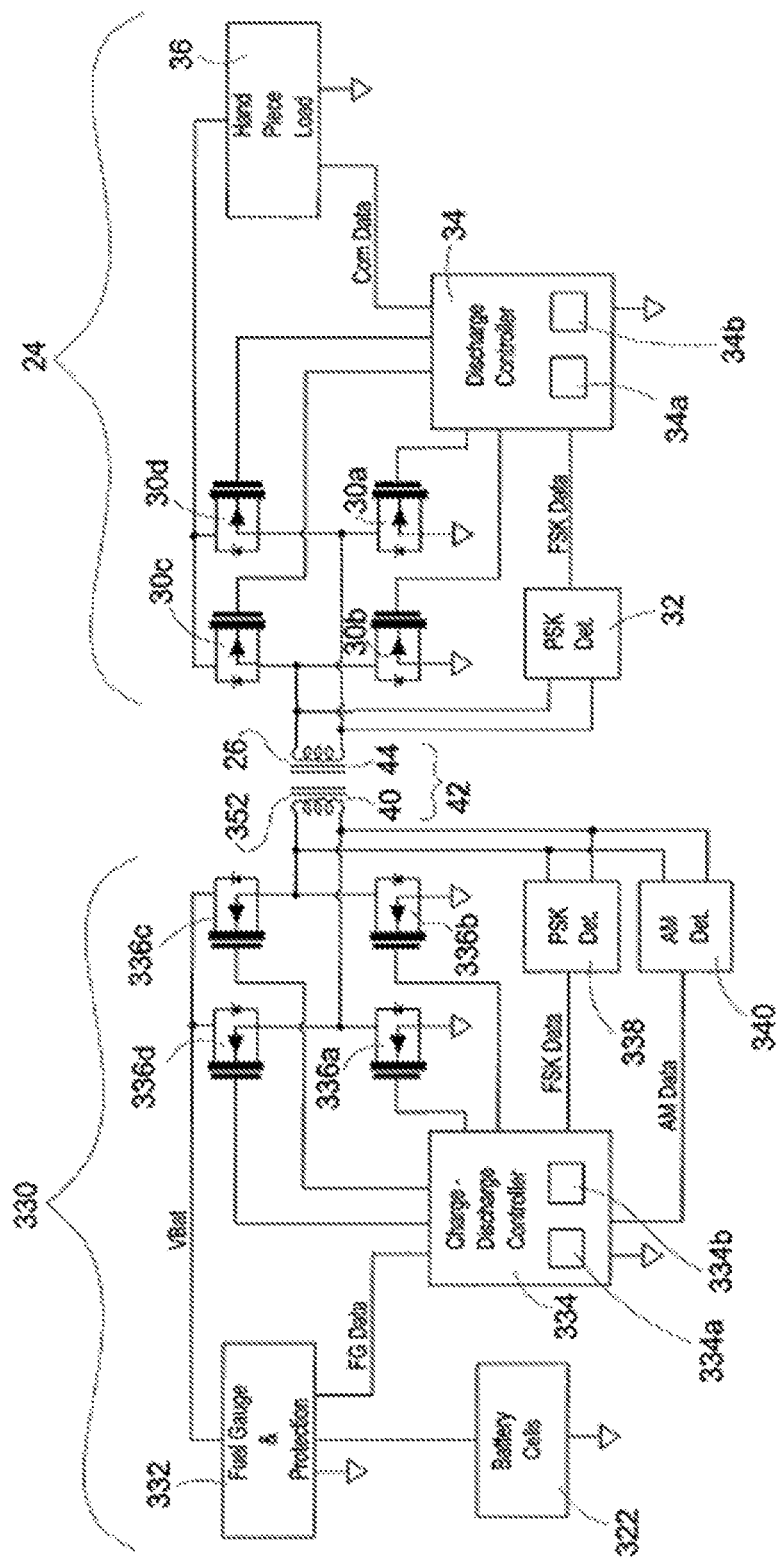
FIG. 7 is a schematic diagram of the circuitry interface between a battery assembly and a surgical instrument in accordance with the surgical system of FIG. 1.
Figure 8:
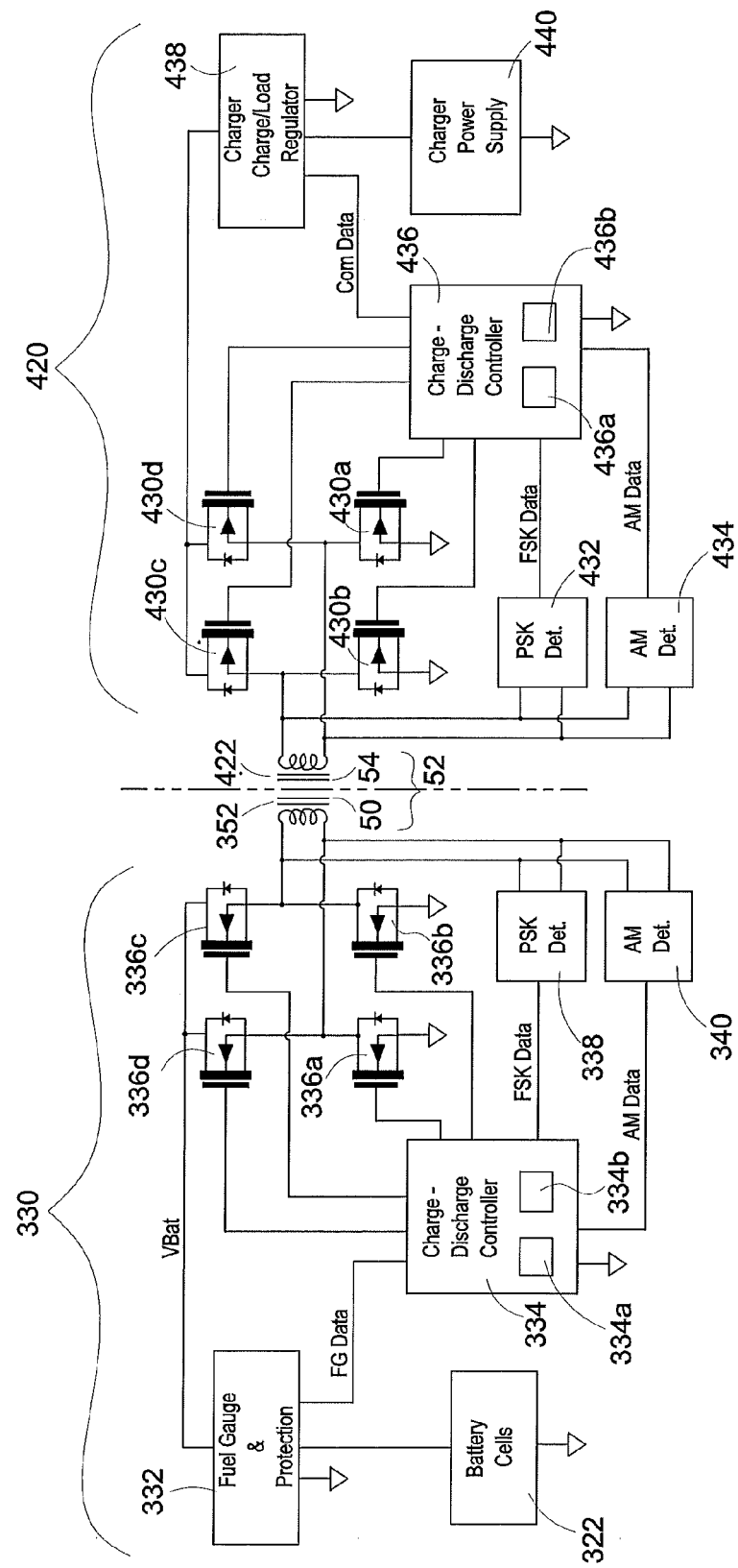
FIG. 8 is a schematic diagram of the circuitry interface between a battery assembly and a battery charger in accordance with the surgical system of FIG. 1.

Referring now to FIGS. 7 and 8, battery circuitry 330 includes fuel gauge and protection circuitry 332, a charge-discharge controller 334, field effect transistors (FETs) 336a-336d, a phase-shift keying (PSK) detector 338, an amplitude modulation (AM) detector 340, and a primary winding 352. Fuel gauge and protection circuitry 332 monitors various battery parameters, e.g., pack impedance, pack temperature, pack voltage, pack current, average current, state of charge, full charge capacity, etc., and provides various safety features, e.g., over and under voltage protection, over current protection, over and under temperature protection, etc. Fuel gauge and protection circuitry 332 also communicates with charge-discharge controller 334 to control the charging and discharging of battery cells 322 across transformers 42 (FIG. 7) and 52 (FIG. 8) via primary winding 352, and provides relevant fuel gauge data, e.g., regarding the state, condition, and/or parameters of battery assembly 300, for transmission across transformers 42 (FIG. 7) and 52 (FIG. 8) via primary winding 352.

Charge-discharge controller 334 includes a processor 334a and memory 334b, e.g., ROM, RAM, or other suitable memory for temporarily or permanently storing information received by controller 334. Charge-discharge controller 334 is configured to communicate with a target device, e.g., a surgical instrument 100 (FIGS. 1 and 2) or a charger 400 (FIGS. 5 and 6), via primary winding 352 as needed to control the transmission and reception of energy for discharging or charging the battery pack 320.

Primary winding 352 is electrically connected to fuel gauge and protection circuitry 332, charge-discharge controller 334, FETs 336a-336d, phase-shift keying (PSK) detector 338, amplitude modulation (AM) detector 340, and battery cells 322. Interface cap 350 includes primary winding 352 which is configured as a first winding 40 (FIG. 7) of a transformer 42 (FIG. 7) to provide an inductive, e.g., wireless, electrical interface between battery assembly 300 and a surgical instrument 20, e.g., electrosurgical instrument 102 (FIG. 1) or ultrasonic instrument 202 (FIG. 2), for transmitting or receiving power, data, and/or control signals therebetween. Primary winding 352 is also configured as a first winding 50 (FIG. 8) of a transformer 52 (FIG. 8) to provide an inductive, e.g., wireless, electrical interface between battery assembly 300 and charger 400 (FIGS. 5 and 6) for transmitting or receiving power, data, and/or control signals therebetween.

FETs 336a-336d are configured in a full bridge topology (although other suitable configurations are also contemplated) to convert the DC voltage from battery cells 322 to AC voltage for output across transformers 42 (FIG. 7) and 52 (FIG. 8) for discharging the battery cells 322 and to convert incoming AC voltage across transformer 52 (FIG. 8) to DC voltage for charging the battery cells 322. For example, FETs 336a-336d are alternately switched on and off in pairs, 336a, 336b and 336c, 336d to generate a power square wave output across transformer 42. FETs 336a-336d may be switched on and off according to clock cycles of the processor 334a of charge-discharge controller 334.

Referring now to FIG. 7, surgical instrument 20 (FIG. 1) includes a battery dock 22 (FIG. 1) configured to receive battery assembly 300 and having device circuitry 24. Device circuitry 24 includes a secondary winding 26 configured as a second winding 44 of transformer 42 when battery assembly 300 is inserted into battery dock 22. Battery dock 22 is configured to receive battery assembly 300 such that primary winding 352 of interface cap 350 aligns with secondary winding 26 of device circuitry 24 to form transformer 42. Battery dock 22 and/or interface cap 350 may include an insulative barrier to insulate the primary and secondary windings 352 and 26 from direct electrical contact, i.e., establishing wireless electrical communication therebetween.

Device circuitry 24 includes a plurality of FETs 30a-30d, a PSK detector 32, and a discharge controller 34. Discharge controller 34 includes a processor 34a and memory 34b similar to charge-discharge controller 334. Secondary winding 26 is electrically connected to FETs 30a-30d, PSK detector 32, and discharge controller 34 which are in turn electrically connected to a hand piece load 36.

FETs 30a-30d are configured in a full bridge topology (although other suitable configurations are also contemplated) to rectify the AC voltage input from transformer 42 to DC voltage for use by the hand piece load 36. For example, FETs 30a-30d are alternately switched on and off in pairs, 30a, 30c and 30b, 30d, to convert the power square wave to DC voltage. FETs 30a-30d may be switched on and off according to clock cycles of the processor 34a of discharge controller 34.

Hand piece load 36 may be any load used by a hand-held surgical device including, for example, an electrosurgical or ultrasonic generator, a motor, control buttons or switches, or other similar hand piece loads 36.

As detailed below, in addition to enabling power transfer from battery assembly 300 to surgical instrument 20, battery circuitry 330 of battery assembly 300 is further configured to perform simultaneous bi-directional communication with device circuitry 24 by using both phase shifting and amplitude modulation on the transferred power square wave signal. That is, by using these two different communication methods, e.g., phase shifting and amplitude modulation, simultaneous bi-directional communication can be achieved. However, although the exemplary embodiments are detailed below with respect to a configuration wherein data transfer from the battery circuitry 330 to the device circuitry 24 is accomplished through phase shifting and wherein data transfer from the device circuitry 24 to the battery circuitry 330 is accomplished through AM modulation, it is also contemplated that this configuration be reversed or that other suitable communication methods be provided for enabling simultaneous bi-directional communication.

During power transfer from battery assembly 300 to surgical instrument 20, charge-discharge controller 334 converts the DC battery voltage from battery cells 322 into an AC power square wave for output across transformer 42 by using FETs 336a-336d as described above. The power square wave may have a frequency of 200 KHz, although other suitable frequencies or frequency ranges are also contemplated, depending on a particular application. For example, low power transfer applications may use higher frequencies to reduce the size of the circuit components, particularly of the transformer. High power transfer applications, on the other hand, may require or desire lower frequencies in order to improve efficiency and/or reduce heating within the battery pack and/or at the hand piece load 36. The discharge controller 34 of device circuitry 24 initially receives power via passive full bridge rectification of the incoming power from transformer 42 and, once initialized, uses FETs 30a-30d to rectify the incoming power with the load 36 and to convert the incoming power back to DC voltage for output to the hand piece load 36, e.g., the generator of the surgical instrument 20. PSK detector 32 functions to monitor the incoming power square wave from transformer 42 to detect if the hand piece load 36 and the incoming power square wave are out of sync. PSK detector 32 also causes the FETs 30a-30d to rectify the phase of the received power square wave to be synchronized with the hand piece load 36 when the incoming power square wave and the hand piece load 36 are out of sync. Data transfer from the battery circuitry 330 to the device circuitry 24 is accomplished through phase shifting of the power square wave. For example, charge-discharge controller 334 of battery circuitry 330 communicates with fuel gauge 332 to obtain fuel gauge data and transmits the fuel gauge data across transformer 42 by phase shifting the power square wave. The PSK detector 32 of device circuitry 24 monitors, cycle by cycle, the incoming power square wave from transformer 42 to detect a phase shift and decodes the data from the phase shift for passing on to the discharge controller 34 for interpretation. As an example, if PSK detector 32 detects an incoming power square wave that is synchronized with the hand piece load 36, the PSK detector 32 outputs a binary output of "0" to discharge controller 34 while if PSK detector 32 detects an incoming power square wave that is phase shifted relative to the hand piece load 36, the PSK detector 32 outputs a binary output of "1" to controller 34. Other methods of decoding data from the phase shift are also contemplated including, for example, outputting a binary output of "1" when there is no phase shift, outputting a binary output of "0" when there is a phase shift, outputting binary outputs of "0" and "1" based on the degree of phase shift where no data is transferred between the battery circuitry 330 and the device circuitry 24 if the power square wave is synchronized with the output load 36, or outputting other values or indicators of the data being extracted to discharge controller 34. To ensure that the phase shifting of the power square wave is properly detected, the clock timing of the charge-discharge controller 334 and the discharge controller 34 may be synchronized upon initialization of power transfer across transformer 42.

Data transfer from the device circuitry 24 to the battery circuitry 330 is accomplished through AM modulation of the power square wave transferred across transformer 42. For example, incoming power load requirements from the hand-piece load 36 can be varied, cycle by cycle, by turning the synchronizing FETs 30a-30d on and off at the power square wave frequency to modulate the resulting current draw and therefore the amplitude of the power square wave output from battery circuitry 330 across transformer 42. By varying the cycle by cycle load requirements, the amplitude of the outgoing power square wave from the battery circuitry 330 side of transformer 42 can be controlled by the device circuitry 24 and data can be transferred from the device circuitry 24 to the battery circuitry 330. The AM detector 340 decodes the data from the changes in amplitude caused by the device circuitry 24 for passing on to the charge-discharge controller 334 for interpretation. For example, detection of an initial or baseline amplitude of the power square wave by AM detector 340 results in an output of a binary "0" to charge-discharge controller 334 while detection of an increased or decreased amplitude by AM detector 340 results in an output of a binary "1" to charge-discharge controller 334. Other methods of decoding data from the amplitude are also contemplated including, for example, outputting a binary output of "1" when the amplitude is at the baseline or initial amplitude, outputting a binary output of "0" when there is an increase or decrease in the amplitude, outputting binary outputs of "0" and "1" based on the degree of amplitude modulation where no data is transferred between the device circuitry 24 and the battery circuitry 330 if the power square wave has the baseline or initial amplitude, or outputting other values or indicators of the data being extracted to charge-discharge controller 334.

During power supply to hand piece load 36, the amplitude of the power square wave may also be modulated by natural fluctuations in the power requirements of the load. To ensure that the data being transferred through amplitude modulation of the power square wave is properly detected, some form of frequency discrimination between the natural power load fluctuations and the desired data modulation is necessary. For example, the power square wave may be used as a data clock to discriminate between the natural load power fluctuations and the desired data modulation. During the transfer of power, the natural load power fluctuations from the hand piece load 36 of the surgical device 20 will typically be an order of magnitude lower in frequency than the cycle to cycle modulation produced by the AM modulation of the power square wave, thus enabling discrimination. Various high pass/low pass filters or tracking mechanisms (not shown) may be employed to adequately discriminate between the low frequency load fluctuations and the high frequency AM data modulation.

Referring now to FIG. 8, charging circuitry 420 of battery charger 400 (FIG. 1) includes a secondary winding 422 within each charging bay 410 configured as a second winding 54 of transformer 52 when battery assembly 300 is inserted into a charging bay 410. Charging bay 410 is configured to receive battery assembly 300 such that primary winding 352 of interface cap 350 aligns with secondary winding 422 of batter charger 400 to form transformer 52.

Charging circuitry 420 includes a plurality of FETs 430a-430d, a PSK detector 432, and AM detector 434, a charge-discharge controller 436, and a charger charge/load regulator 438. Charge-discharge controller 436 includes a processor 436a and memory 436b similar to charge-discharge controller 334. Secondary winding 422 is electrically connected to FETs 430a-430d, PSK detector 432, AM detector 434, charge-discharge controller 436, and charger charge/load regulator 438. Charger charge/load regulator 438 is in turn electrically connected to a charger power supply 440 which is in turn connected to a source of electrical energy such as, for example, a wall outlet (mains supply). Charger power supply 440 provides a DC voltage to charging circuitry 420.

Charger 400 and battery circuitry 330 cooperate to enable charging and discharging of battery cells 322 and performance of continuous bi-directional simultaneous communication during both charging and discharging by using both phase shifting and amplitude modulation on the transferred power square wave signal, similarly as detailed above with respect to battery circuitry 330 and surgical instrument 20.

During a charging cycle, power is transferred from charger 400 to battery assembly 300 to charge battery cells 322. Charger 400 receives DC voltage from charger power supply 440 and charge-discharge controller 436 converts the DC voltage from charger power supply 440 into an AC power square wave for output across transformer 52 by using FETs 430a-430d in a similar manner to FETs 336a-336d as described above for battery circuitry 300. The charge-discharge controller 334 of battery circuitry 300 uses FETs 336a-336d to rectify the incoming power square wave back to DC voltage for storing in the battery cells 322. PSK detector 338 functions to monitor the incoming power square wave from transformer 52 to detect if the load from the battery cells 322 and the incoming power square wave are out of sync. PSK detector 338 also rectifies the phase of the received power square wave to be synchronized with the load from the battery cells 322.

Data transfer from the charger circuitry to the battery circuitry 330 during charging of battery cells 322 is accomplished through phase shifting of the power square wave. Alternatively, this data transfer may be accomplished using AM modulation, with the transfer of data from battery circuitry 330 to charger circuitry 420 being accomplished using phase shifting. Charge-discharge controller 436 of charger circuitry 420, for example, communicates with charger charge/load regulator 438 to obtain charging data and transmits the charging data across transformer 52 by phase shifting the power square wave. The PSK detector 338 of battery circuitry 330 monitors the incoming power square wave from transformer 52 to detect the phase shift and decodes the data from the phase shift for passing on to the charge-discharge controller 334 for interpretation. As an example, if PSK detector 334 detects an incoming power square wave that is synchronized with the load of the battery cells 322, the PSK detector 338 outputs a binary output of "0" to charge-discharge controller 334 while if PSK detector 338 detects an incoming power square wave that is phase shifted relative to the load of the battery cells 322, the PSK detector 338 outputs a binary output of "1" to charge-discharge controller 334. Other methods of decoding data from the phase shift are also contemplated including, for example, outputting a binary output of "1" when there is no phase shift, outputting a binary output of "0" when there is a phase shift, outputting binary outputs of "0" and "1" based on the degree of phase shift where no data is transferred between the charger circuitry 420 and the battery circuitry 330 if the power square wave is synchronized with the load of the battery cells 322, or outputting other values or indicators of the data to extracted to charge-discharge controller 334. To ensure that the phase shifting of the power square wave is properly detected, the clock timing of the charge-discharge controller 436 and the charge-discharge controller 334 may be synchronized upon initialization of power transfer across transformer 52.

Data transfer from the battery circuitry 330 to the charger circuitry 420 during charging of battery cells 322 is accomplished through AM modulation of the power square wave transferred across transformer 52 although, as mentioned above, other configurations are also contemplated. Incoming power load requirements from the battery cells 322 can be varied, for example, by turning the synchronizing FETs 336a-336d on and off at the power square wave frequency to adjust the required amplitude of the power square wave output from charger circuitry 420 across transformer 52. By varying the load requirements, the amplitude of the outgoing power square wave from the charger circuitry 420 side of transformer 52 can be controlled by the battery circuitry 330 and data can be transferred from the battery circuitry 330 to the charger circuitry 420. The AM detector 434 decodes the data from the changes in amplitude caused by the battery circuitry 330 for passing on to the charge-discharge controller 436 for interpretation. For example, detection of an initial or baseline amplitude of the power square wave by AM detector 434 results in an output of a binary "0" to charge-discharge controller 436 while detection of an increased or decreased amplitude by AM detector 434 results in an output of a binary "1" to charge-discharge controller 436. Other methods of decoding data from the amplitude are also contemplated including, for example, outputting a binary output of "1" when the amplitude is at the baseline or initial amplitude, outputting a binary output of "0" when there is an increase or decrease in the amplitude, outputting binary outputs of "0" and "1" based on the degree of amplitude modulation where no data is transferred between the battery circuitry 330 and the charger circuitry 420 if the power square wave has the baseline or initial amplitude, or outputting other values or indicators of the data being extracted to charge-discharge controller 436.

During a discharge cycle, power is transferred from battery assembly 300 to charger 400 to discharge battery cells 322. Battery circuitry 330 receives DC voltage from battery cells 322 and charge-discharge controller 334 converts the DC voltage from battery cells 322 into an AC power square wave for output across transformer 52 by using FETs 336a-336d as described above for output across transformer 42. The charge-discharge controller 436 of charger circuitry 420 uses FETs 430a-430d to rectify the incoming power square wave back to DC voltage for discharge through charger charge/load regulator 438 and charger power supply 440. PSK detector 432 functions to monitor the incoming power square wave from transformer 52 to detect if the load from the charger charge/load regulator 438 and the incoming power square wave are out of sync. PSK detector 432 also rectifies the phase of the received power square wave to be synchronized with the load from the charger charge/load regulator 438.

Data transfer from the battery circuitry 330 to the charger circuitry 420 during discharging of battery cells 322 is accomplished through phase shifting of the power square wave. Alternatively, this data transfer may be accomplished using AM modulation, with the transfer of data from charger circuitry 420 to battery circuitry 330 being accomplished using phase shifting. Charge-discharge controller 334 of battery circuitry 330, for example, communicates with fuel gauge 332 to obtain fuel gauge data and transmits the fuel gauge data across transformer 52 by phase shifting the power square wave. The PSK detector 432 of charger circuitry 420 monitors the incoming power square wave from transformer 52 to detect the phase shift and decodes the data from the phase shift for passing on to the charge-discharge controller 436 for interpretation. As an example, if PSK detector 432 detects an incoming power square wave that is synchronized with the load of the charger charge/load regulator 438, the PSK detector 432 outputs a binary output of "0" to charge-discharge controller 436 while if PSK detector 432 detects an incoming power square wave that is phase shifted relative to the load of the charger charge/load regulator 438, the PSK detector 432 outputs a binary output of "1" to charge-discharge controller 436. Other methods of decoding data from the phase shift are also contemplated including, for example, outputting a binary output of "1" when there is no phase shift, outputting a binary output of "0" when there is a phase shift, outputting binary outputs of "0" and "1" based on the degree of phase shift where no data is transferred between the battery circuitry 330 and the charger circuitry 420 if the power square wave is synchronized with the load of the charger charge/load regulator 438, or outputting other values or indicators of the data being extracted to charge-discharge controller 436. To ensure that the phase shifting of the power square wave is properly detected, the clock timing of the charge-discharge controller 334 and the charge-discharge controller 436 may be synchronized upon initialization of power transfer across transformer 52.

Data transfer from the charger circuitry 420 to the battery circuitry 330 during discharging of battery cells 322 is accomplished through AM modulation of the power square wave transferred across transformer 52 although, as mentioned above, other configurations are also contemplated. For example, incoming power load requirements from the load of the charger charge/load regulator 438 can be varied by turning the synchronizing FETs 430a-430d on and off at the power square wave frequency to adjust the required amplitude of the power square wave output from battery circuitry 330 across transformer 52. By varying the load requirements, the amplitude of the outgoing power square wave from the battery circuitry 330 side of transformer 52 can be controlled by the charger circuitry 420 and data can be transferred from the charger circuitry 420 to the battery circuitry 330. The AM detector 340 decodes the data from the changes in amplitude caused by the charger circuitry 420 for passing on to the charge-discharge controller 334 for interpretation. For example, detection of an initial or baseline amplitude of the power square wave by AM detector 340 results in an output of a binary "0" to charge-discharge controller 334 while detection of an increased or decreased amplitude by AM detector 340 results in an output of a binary "1" to charge-discharge controller 334. Other methods of decoding data from the amplitude are also contemplated including, for example, outputting a binary output of "1" when the amplitude is at the baseline or initial amplitude, outputting a binary output of "0" when there is an increase or decrease in the amplitude, outputting binary outputs of "0" and "1" based on the degree of amplitude modulation where no data is transferred between the charger circuitry 420 and the battery circuitry 330 if the power square wave has the baseline or initial amplitude, or outputting other values or indicators of the data being extracted to charge-discharge controller 334.

Battery assembly 300 includes two rest states and two active states. Battery assembly 300 is initially configured for shipping in a powered down state, also known as a ship mode. In ship mode, the battery assembly 300 is dormant with the fuel gauge 332 shut down and no power provided to the charge-discharge controller 334. Battery assembly 300 may only be activated from ship mode by placing battery assembly 300 in charger 400.

Once battery assembly 300 has been placed in charger 400 the first time, the supply of power from charger to battery assembly 300 "wakes up" battery assembly 300 from the ship mode and, as a result, battery assembly 300 enters a charge mode. In the charge mode, battery assembly 300 is awake and communicating with charger 400 to accept power from charger 400 as described above. When charging is complete or battery assembly 300 is removed from charger 400 (and after expiration of a delay period, in some embodiments), battery assembly 300 enters a sleep mode. Subsequent placement of the battery assembly 300 in charger 400 wakes up the battery assembly 300 from sleep mode and places the battery assembly 300 in either charge or discharge mode depending on the desired function.

In sleep mode, battery assembly 300 is dormant with fuel gauge 332 waking up periodically to check on the status of the battery assembly 300. Unlike a conventional battery assembly which uses electrical contacts to complete a circuit for determining when to wake up, the use of a transformer for power transfer requires periodic pinging of the primary winding 352 to determine if a load is present. To this end, fuel gauge 332 wakes up the charge-discharge controller 334 and asks the charge-discharge controller 334 to check if an external load is present. The charger-discharge controller 334 pings the primary winding 352 to look for a suitable external load such as, for example, handpiece load 36 or the load of charger charge/load regulator 438. If a load is present across transformer 42 or 52, the battery assembly 300 enters a discharge mode. During the discharge mode, the battery assembly 300 is awake and transmits power to the handpiece load 36 or the load of the charger charge/load regulator 438. Other suitable loads for use with battery assembly 300 are also contemplated. If a load is present across transformer 52, the battery assembly 300 may alternatively enter the charge mode as described above.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical system, comprising:
a surgical instrument; and
a battery assembly, including battery circuitry, removably coupled to the surgical instrument and configured to wirelessly transfer electrical power to the surgical instrument, the surgical instrument and the battery assembly configured for simultaneous bi-directional communication of data via the transferred electrical power,
wherein the battery circuitry is configured to transmit data to the surgical instrument by using a first transmission protocol and receive data from a device by using a second transmission protocol.

2. The surgical system according to claim 1, wherein the battery assembly includes a first winding and the surgical instrument includes a second winding, the first and second windings together forming a transformer for transferring the electrical power from the battery assembly to the surgical instrument when the battery assembly is coupled to the surgical instrument.

3. The surgical instrument according to claim 1, wherein the communication of data in a direction from the battery assembly to the surgical instrument is performed by adjusting the transferred electrical power in a first manner and wherein the communication of data in a direction from the surgical instrument to the battery assembly is performed by adjusting the transferred electrical power in a second, different manner.

4. The surgical system according to claim 3, wherein the battery assembly is configured to transmit data to the surgical instrument in the first manner by shifting a phase of the transferred electrical power, the surgical instrument configured to detect the phase shift and decode the transmitted data from the phase shift.

5. The surgical system according to claim 4, wherein the surgical instrument includes a phase-shift keying detector for detecting the phase shift of the transferred electrical power.

6. The surgical system according to claim 3, wherein the surgical instrument is configured to transmit data to the battery assembly in the second manner by modulating an amplitude of the transferred electrical power, the battery assembly configured to detect the modulated amplitude and decode the transmitted data from the modulated amplitude of the transferred electrical power.

7. The surgical system according to claim 6, wherein the battery assembly includes an amplitude modulation detector for detecting the amplitude modulation of the transferred electrical power.

8. The surgical system according to claim 1, wherein the transferred electrical power is a power square wave.

9. The surgical system according to claim 1, further including a battery charger, the battery assembly removably couplable to the battery charger and configured to at least one of wirelessly transfer electrical power to the battery charger and wirelessly receive electrical power from the battery charger, the battery charger and the battery assembly configured for simultaneous bi-directional communication of data via the transferred or the received electrical power.

10. The surgical system according to claim 1, wherein the battery assembly includes a first winding and the battery charger includes a second winding, the first and second windings together forming a transformer for transferring the electrical power from the at least one of the battery assembly to the battery charger and the battery charger to the battery assembly when the battery assembly is coupled to the battery charger.

11. A battery assembly couplable to a target device, the battery assembly comprising:
- at least one battery cell;
- a first winding electrically connected to the at least one battery cell and alignable relative to a second winding of the target device to form a transformer therewith; and
- battery circuitry electrically connected to the at least one battery cell and the first winding and configured to control at least one of the transfer of electrical power from the at least one battery cell across the transformer to the target device and the reception of electrical power from the target device across the transformer to the at least one battery cell, the battery circuitry configured for simultaneous bi-directional communication of data with the target device via the transferred or received electrical power,
- wherein the battery circuitry is configured to transmit data to the target device by using a first transmission protocol and receive data from the target device by using a second transmission protocol.

12. The battery assembly according to claim 11, wherein the battery circuitry is configured to transmit data to the target device by shifting a phase of the transferred electrical power.

13. The battery assembly according to claim 11, wherein the battery circuitry is configured to transmit data to the target device by modulating the amplitude of the received electrical power.

14. The battery assembly according to claim 11, wherein the battery circuitry is configured to receive data from the target device by detecting a phase shift of the received electrical power and decoding the data from the detected phase shift.

15. The battery assembly according to claim 14, wherein the battery circuitry includes a phase-shift keying detector for detecting the phase shift of the received electrical power.

16. The battery assembly according to claim 11, wherein the battery circuitry is configured to receive data from the target device by detecting an amplitude modulation of the transferred electrical power and decoding the data from the detected amplitude modulation.

17. The battery assembly according to claim 16, wherein the battery circuitry includes an amplitude modulation detector for detecting the amplitude modulation of the transferred electrical power.

18. The surgical system according to claim 11, wherein the transferred electrical power and the received electrical power are power square waves.

19. The surgical system according to claim 11, wherein the target device is selected from a group consisting of a surgical instrument and a battery charger.

20. A method of simultaneous bi-directional communication between a battery assembly and a target device, the method comprising:
- coupling the battery assembly to the target device;
- wirelessly transferring electrical power from one of the battery assembly and the target device to the other of the battery assembly and the target device; and
- simultaneously transmitting data from the battery assembly to the target device and from the target device to the battery assembly via the transferred electrical power by:
  - phase shifting the transferred electrical power by the one of the battery assembly and the target device;
  - amplitude modulating the transferred electrical power by the other of the battery assembly and the target device;
  - detecting the phase shifting of the transferred electrical power by the other of the battery assembly and the target device; and
  - detecting the amplitude modulation of the transferred electrical power by the one of the battery assembly and the target device.

* * * * *